(12) United States Patent
Batzinger et al.

(10) Patent No.: US 9,404,903 B2
(45) Date of Patent: Aug. 2, 2016

(54) METHOD FOR PIPELINE INSPECTION

(71) Applicant: PII LIMITED, Cramlington, Northumberland (GB)

(72) Inventors: Thomas James Batzinger, Burnt Hills, NY (US); Jeffrey Earle Sutherland, Calgary (CA); Ruediger Bauernschmitt, Linkenheim-Hochstett (DE); Achim Hugger, Stutensee (DE); David Martin Paige, Newcastle-Upon-Tyne (GB)

(73) Assignee: PII Limited, Northumberland (GB)

( * ) Notice: Subject to any disclaimer, the term of this patent is extended or adjusted under 35 U.S.C. 154(b) by 786 days.

(21) Appl. No.: 13/683,343

(22) Filed: Nov. 21, 2012

(65) Prior Publication Data

US 2013/0125654 A1    May 23, 2013

(30) Foreign Application Priority Data

Nov. 22, 2011    (EP) .................................... 11190178

(51) Int. Cl.
*G01N 29/265* (2006.01)
*G01N 33/00* (2006.01)
(Continued)

(52) U.S. Cl.
CPC ............... *G01N 33/00* (2013.01); *G01M 3/005* (2013.01); *G01M 3/246* (2013.01); *G01N 29/04* (2013.01); *G01N 29/043* (2013.01); *G01N 29/2412* (2013.01); *G01N 2291/2636* (2013.01)

(58) Field of Classification Search
CPC . G01N 33/00; G01N 29/043; G01N 29/2412; G01N 29/265; G01N 29/262; G01N 29/04; G01N 29/24; G01N 2291/2636; G01N 2291/02854; G01N 2291/0289; G01M 3/005; G01M 3/243; G01M 3/246

USPC .................................... 73/623, 622, 601, 643
See application file for complete search history.

(56) References Cited

U.S. PATENT DOCUMENTS

| 3,868,847 A | 3/1975 | Gunkel |
| 4,375,165 A | 3/1983 | de Sterke |

(Continued)

FOREIGN PATENT DOCUMENTS

| EP | 2031385 A1 | 4/2009 |
| WO | 03/021249 A2 | 3/2003 |

(Continued)

OTHER PUBLICATIONS

European Search Report and Written Opinion dated Mar. 29, 2012 which was issued in connection with the EP Patent Application No. 11190178.1 which was filed on Nov. 22, 2011.

(Continued)

*Primary Examiner* — Daniel S Larkin
*Assistant Examiner* — Rose M Miller
(74) *Attorney, Agent, or Firm* — GE Global Patent Operation

(57) ABSTRACT

A method for pipeline inspection is provided. The method includes carrying out an inspection run in which a pipeline inspection apparatus travels inside a pipeline, wherein sensors on the apparatus are configured to conduct an in-line inspection of wall material along a length of the pipeline. The method includes initiating a first inspection mode to produce a primary inspection data set, wherein the first inspection mode comprises an inspection of the pipeline wall material upstream and downstream of a location of a dented region in the pipeline, selectively initiating a second inspection mode to produce a secondary inspection data set, wherein the second inspection mode includes an inspection of the pipeline wall material in the dented region in the length of the pipeline, and combining the primary and the secondary inspection data sets to provide a direct assessment for the presence of cracks and/or corrosion in wall material along the pipeline.

13 Claims, 3 Drawing Sheets

(51) Int. Cl.
    *G01N 29/04* (2006.01)
    *G01M 3/00* (2006.01)
    *G01M 3/24* (2006.01)
    *G01N 29/24* (2006.01)

(56) References Cited

U.S. PATENT DOCUMENTS

| | | | |
|---|---|---|---|
| 6,474,165 B1 | 11/2002 | Harper et al. | |
| 6,847,207 B1* | 1/2005 | Veach et al. | 324/220 |
| 7,474,092 B1 | 1/2009 | Kwun et al. | |
| 2004/0095137 A1* | 5/2004 | Kwun et al. | 324/240 |
| 2005/0072237 A1 | 4/2005 | Paige et al. | |
| 2008/0143344 A1 | 6/2008 | Focia et al. | |
| 2009/0101337 A1* | 4/2009 | Neidhardt | 166/250.01 |
| 2010/0313665 A1* | 12/2010 | Chougrani et al. | 73/623 |

FOREIGN PATENT DOCUMENTS

| | | |
|---|---|---|
| WO | 2009087342 A1 | 7/2009 |
| WO | 2010046685 A1 | 4/2010 |

OTHER PUBLICATIONS

Wolf: "Rohrleitungsinspektionen nach dem Ultraschallverfahren—Pipeline Inspections using Ultrasonic Methods" 3R International, Vulkan-Verlag, Essen, Germany, vol. 40, No. 6, Jun. 1, 2001.

* cited by examiner

METHOD FOR PIPELINE INSPECTION

BACKGROUND OF THE INVENTION

Embodiments of the present invention relate to a method for pipeline inspection, and more particularly, a method for in-line detection of anomalies such as cracks and/or corrosion in or near dented regions of a pipeline.

It is known to carry out inspection of a pipeline using an inspection apparatus (commonly referred to as a pipeline "pig"), which travels inside the pipeline and includes inspection sensors arranged for measuring or detecting defects in the wall of the pipeline.

Many conventional in-line inspection techniques require accurate mechanical alignment of inspection sensors with respect to the pipe wall in order to maintain a suitable level of inspection sensitivity. A problem occurs if the pipeline includes a dented region or other physical anomaly. A significant factor is that pipeline dents tend to have an arbitrary shape and are difficult for inspection apparatus to negotiate mechanically. This mechanical difficulty can translate into an inspection difficulty, particularly if desired alignment between the inspection sensors and the surface under inspection is compromised as the apparatus passes through a dented region at speed.

It is not uncommon, therefore, for the general location of a dented region within a pipeline to be identified and then classified as a region of limited inspection, due to the potential unreliability of inspection data from that location.

Otherwise, it is known to use a dimensional tool to determine the specific geometry of a particular dent, and to then carry out a probability analysis for the likely presence of cracks or corrosion as a function of the specific geometry. However, it will be understood that such indirect analysis techniques are prone to error and may even leave potentially serious defects undetected.

A method for pipeline inspection which overcomes or mitigates one or more of the above problems, or other disadvantages or problems associated with conventional methods for inline inspection of pipelines would be desirable.

BRIEF DESCRIPTION OF THE INVENTION

According to an embodiment of the present invention, a method for pipeline inspection is provided. The method comprises providing a pipeline inspection apparatus configured for operating multiple inspection modes using sensors on the apparatus to provide inspection data relating to the presence of cracks and/or corrosion in wall material of a pipeline; carrying out an inspection run in which a pipeline inspection apparatus travels inside a pipeline, wherein sensors on the apparatus are configured to conduct an in-line inspection of wall material along a length of the pipeline; under normal operating conditions, using a first inspection mode to provide a primary inspection data set for the pipeline wall material upstream and downstream of a location of a dented region; selectively triggering a second inspection mode to provide a second inspection data set for the pipeline wall material as the apparatus travels through a dented region in the length of the pipeline; and combining the primary inspection data set and the second inspection data set to provide a direct assessment for the presence of cracks and/or corrosion in wall material along the length of the pipeline, including along said dented region.

According to an embodiment of the present invention, an apparatus for pipeline inspection configured to travel inside a pipeline is provided. The apparatus comprises sensors for detecting the presence of cracks and/or corrosion in wall material of a pipeline, wherein the apparatus is configured with primary and secondary operating modes, wherein the primary operating mode uses a first mode of inspection to provide primary inspection data from the sensors, relating to the presence of cracks and/or corrosion in wall material along a length of pipeline, and wherein the secondary operating mode uses a second mode of inspection, different to said first mode of inspection, to provide secondary inspection data from the sensors relating to the presence of cracks and/or corrosion in wall material along an axial length of pipeline, and wherein, if the primary operating mode is active, the apparatus is configured to trigger the secondary operating mode in response to a signal indicative that the apparatus is approaching a dented region within a pipeline, and to deactivate the secondary operating mode in response to a signal indicative that the apparatus has travelled beyond said dented region.

These and other aspects and advantages of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and, unless otherwise indicated, they are merely intended to conceptually illustrate the structures and procedures described herein.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION OF EXEMPLARY EMBODIMENTS OF THE INVENTION

The following description of the exemplary embodiments refers to the accompanying drawings. The same reference numbers in different drawings identify the same or similar elements. The following detailed description does not limit the invention. Instead, the scope of the invention is defined by the appended claims.

Reference throughout the disclosure to an exemplary embodiment, an embodiment, or variations thereof means that a particular feature, structure, or characteristic described in connection with an embodiment is included in at least one embodiment of the subject matter disclosed. Thus, the appearance of the phrases in an exemplary embodiment, in an embodiment, or variations thereof in various places throughout the disclosure is not necessarily referring to the same embodiment. Further, the particular features, structures or characteristics may be combined in any suitable manner in one or more embodiments.

Figure 1:
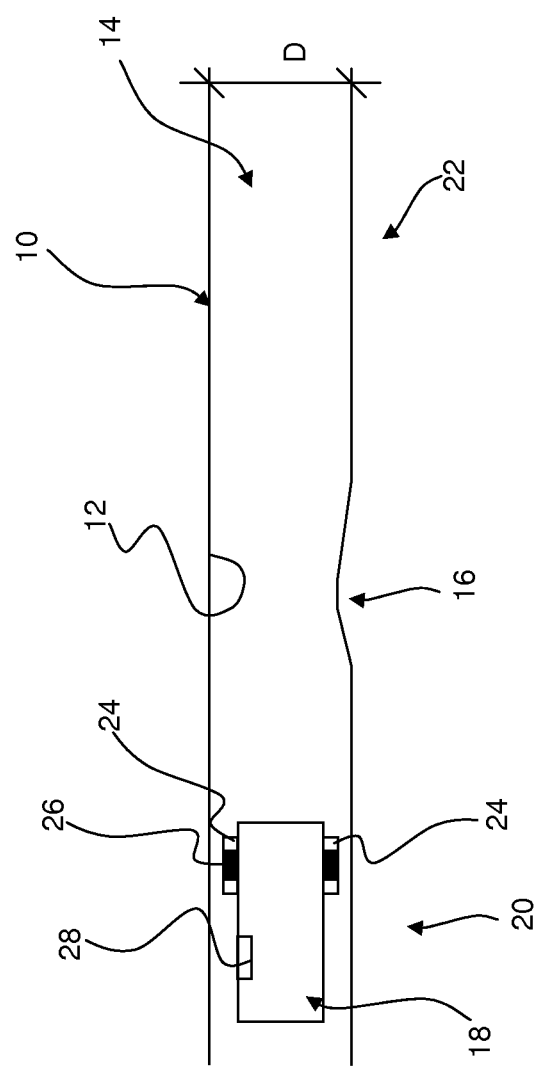
FIG. 1 is a schematic cross section through part of a pipeline having a dented region and an inline inspection apparatus including sensors for detecting cracks and/or corrosion in the material of the pipe wall.

Part of a pipeline 10 is shown schematically in FIG. 1. The pipeline 10 has a wall 12 which defines a bore 14 with an internal diameter D. The pipeline 10 includes a dented region 16.

A pipeline inspection apparatus or "pig" is indicated generally at 18. The apparatus 18 is configured to travel inside the pipeline 10, e.g. between a first location 20 and a second location 22, for inspection purposes. As such, the apparatus 18 includes sensors for detecting the presence of cracks and/or corrosion in the material of the wall 12. More particularly, the apparatus 16 of this exemplary embodiment includes ultrasonic probes 24 configured with one or more transducers 26 for a) introducing ultrasound to the material of the pipe wall 12, and b) receiving return ultrasound to provide inspection data for determining the presence of cracks and/or corrosion in the material of the pipe wall 12.

In use, the apparatus 18 travels along the inside of the pipeline 10 between a first location 20 and a second location 22, and inspection data is recorded relating to characteristics of the wall material between said locations 20, 22.

Conventional modes of ultrasonic inspection require accurate mechanical alignment of transducers 26 on the probes 24 with respect to the pipe wall 12, in order to maintain a suitable level of inspection sensitivity. However, the dented region 16 may have an arbitrary shape, and/or may be difficult for the inspection apparatus 10 to negotiate past mechanically on its path downstream. This may often translate into an inspection difficulty, e.g. if the orientation of the transducers 26 relative to the internal surface of the wall 12 in the dented region 16 becomes misaligned as the apparatus 18 passes through the dented region 16 at speed. Hence, there may be occasions in which the apparatus 18 is incapable of providing detailed inspection data for one or more portions of the wall 12, particularly in or adjacent a dented region 16 or other physical anomaly along the pipeline.

In order to address this problem, a new method of pipeline inspection is proposed.

The apparatus 18 is configured to operate a primary operating mode and a secondary operating mode. In the primary operating mode, the probe 24 operates a first mode of inspection, from which a set of primary inspection data is obtained from the transducers 26 (relating to the presence of cracks and/or corrosion in wall material of an axial length of pipeline along which the apparatus has travelled). Similarly, in the secondary operating mode, the probe 24 operates a second mode of inspection, different from said first mode of inspection, from which a set of secondary inspection data is obtained from the transducers 26, (relating to the presence of cracks and/or corrosion in wall material of an axial length of pipeline along which the apparatus has travelled).

More particularly, the apparatus 18 is configured so that, if the primary operating mode is active, the secondary operating mode is triggered in response to a signal indicative that the apparatus 18 is approaching a dented region 16 within said axial length of pipeline. Furthermore, the secondary operating mode is deactivated in response to a signal indicative that the apparatus 18 has travelled beyond said dented region 16. Hence, the secondary inspection data is related specifically to characteristics of the pipe wall material in and adjacent the dented region 16, whereas the primary inspection data relates to characteristics of the pipe wall material at least upstream and downstream of said dented region 16.

Exemplary embodiments may maintain said primary operating mode when said secondary operating mode is triggered, or may switch from said primary operating mode to said secondary operating mode and back again as the apparatus travels through a dented region. In each case, said primary and secondary inspection data can be combined to provide a direct assessment of the presence of cracks and/or corrosion in wall material along said axial length of pipeline, including along said dented region.

In exemplary embodiments, an on-board controller 28 is used to control operation of the probe 24, in particular to activate and deactivate said secondary operating mode, e.g. dependent upon the relative location of the apparatus 18 along the pipeline 10 with respect to a dented region 16.

Any suitable sensor arrangement(s) may be used for implementing said first and second inspection modes, provided that the second inspection mode is less sensitive to geometric effects than the first inspection mode.

In exemplary embodiments, the probe 24 includes a phased array of ultrasound transducers 26, which is used for said primary operating mode. The first mode of inspection utilizes a conventional phased array propagation of ultrasound within the material of the pipe wall. This will typically involve a refracted shear wave which is reflected back from the pipe wall 12 to the phased array of transducers 26 on the probe 24. In the absence of dents or other significant physical anomalies in the pipe wall, the transducers 26 on the probe 24 will be arranged at a generally desired orientation to the pipe wall 12, and so the integrity of the recorded data will be sound.

In exemplary embodiments, the probe 24 includes an array of transducers 26 configured to introduce ultrasound to the material of the pipe wall 12 as a guidedwave propagation. This represents a mode of inspection that has a longer range and is less sensitive to geometric anomalies (e.g. occurring due to dents) than conventional phased array propagation. Hence, this mode of inspection may be used in said secondary operating mode of exemplary embodiments. The same sensor arrangement may be used to implement both inspection modes. For example, the phased array may be configured to deliver said first and second inspection modes. However, in an exemplary embodiment, the apparatus includes at least one electro-magnetic acoustic transducer (EMAT) for generating guidedwaves for said secondary inspection mode.

Figure 2:
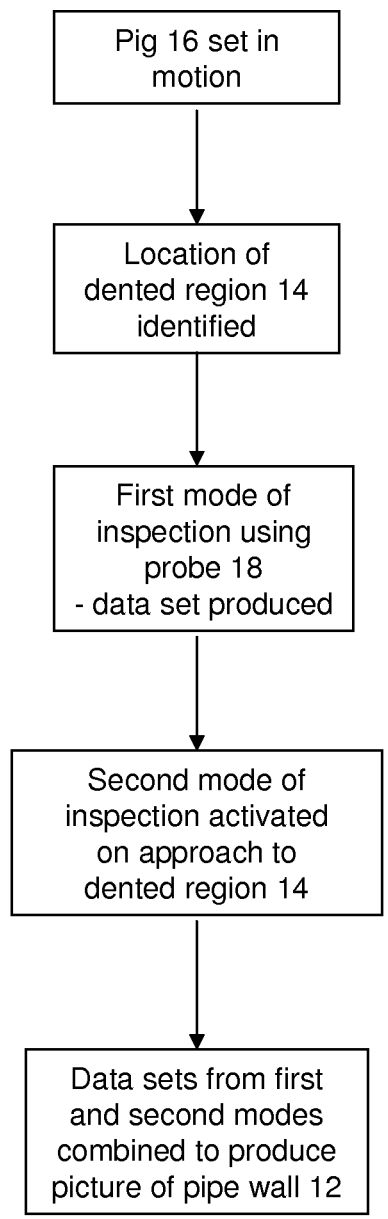
FIG. 2 is a flow diagram outlining an exemplary method of the disclosure.

A flow diagram is shown in FIG. 2, to illustrate an exemplary method of the disclosure.

Firstly, the apparatus 18 is set in motion on an in-line inspection run, i.e. travelling along the bore 14 of the pipeline 10.

The location of the dented region 14 is identified, e.g. using any suitable mechanism or sensor for in-line detection of dents or other physical anomalies in a pipeline. Said mechanism or sensor may form part of the apparatus 18, or may be provided on a separate tool or apparatus travelling ahead of the apparatus 18.

Under normal operating conditions, the apparatus 18 utilizes the primary operating mode, wherein the probe 24 operates said first mode of inspection. Accordingly, a set of primary inspection data is obtained from the transducers 26, relating to the presence of cracks and/or corrosion in the wall material for undented regions of the pipeline.

As the apparatus 18 approaches the location of a dented region 16, the secondary operating mode is triggered and then deactivated only after the apparatus 18 has passed beyond the location of the dented region 16. Accordingly, a set of secondary inspection data is obtained from the transducers 26, relating specifically to the presence of cracks and/or corrosion in the wall material in and immediately adjacent the dented region 16 (upstream and downstream).

In exemplary embodiments, the controller 28 is used to control activation and deactivation of said secondary operating mode, e.g. in response to a signal indicative that the apparatus 18 is approaching or has passed beyond the detected location of the dented region 16.

Said primary and secondary inspection data can be combined, e.g. on-line or off-line, to provide a direct assessment of the presence of cracks and/or corrosion in wall material along a length of the pipeline 10 including said dented region 16.

Figure 3:
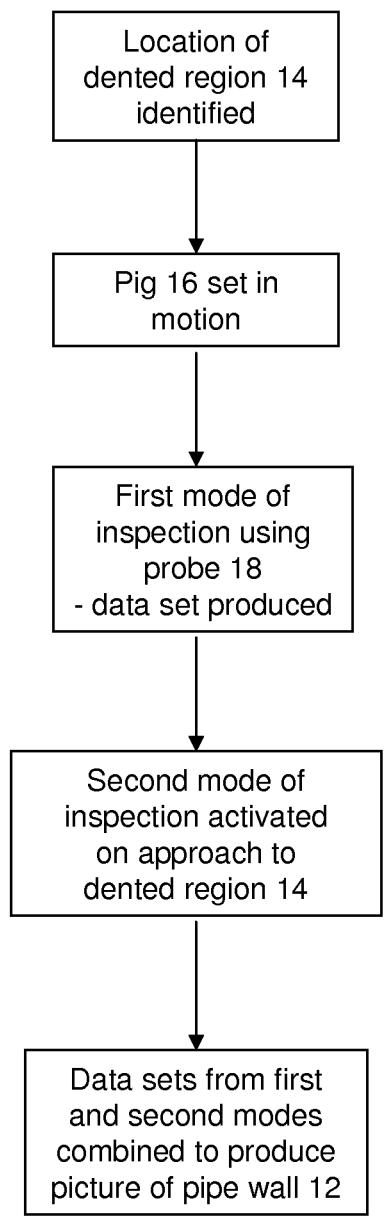
FIG. 3 is a flow diagram outlining an exemplary method of the disclosure.

FIG. 3 is similar to FIG. 2. However, in this exemplary method of the disclosure, the location of the dented region is determined by any suitable means independently of the inspection run of the apparatus 18. Hence, the apparatus may be programmed with data relating to the specific location of one or more dented regions in the pipeline, and further programmed to activate the secondary inspection mode when it is determined that the apparatus 18 is approaching said programmed locations.

The exemplary methods combine different modes of inspection, e.g. short and long range inspection modes, to provide improved inspection of pipelines having one or more dented regions. It will be understood that conventional long range inspection modes provide less detailed data but, unlike short range or close proximity inspection modes (such as conventional phased array techniques), they are generally insensitive to the effects of dent geometry and, hence, advantageously suited for use as said second mode of inspection.

Although described above with respect to a phased array of ultrasonic transducers and at least one electro-magnetic acoustic transducer (EMAT), any suitable sensor arrangement(s) may be used for implementing said first and second inspection modes, provided that the second inspection mode is less sensitive to the geometric effects associated with dented regions than the first inspection mode. In exemplary embodiments, the apparatus may include a leading sensor arrangement and a trailing sensor arrangement, wherein said leading sensor arrangement can be used to trigger the second inspection mode in said trailing sensor arrangement.

The location of dented regions within the pipeline can be achieved via any suitable means, either as part of the same inspection run or an earlier inspection of the pipeline. Similarly, activation and deactivation of said secondary operating mode may be achieved via any suitable means. In exemplary embodiments, data from the sensors may provide the trigger for activation and deactivation of the second operating mode.

According to exemplary methods of the disclosure, two data sets are produced and combined to provide a more accurate picture of the state of the material in the pipe wall, particularly in the dented region(s). The two inspection modes can be operated concurrently as the apparatus passes through the dented region, to provide overlapping inspection data for the pipe wall in and immediately adjacent the dented region (upstream and downstream).

Any suitable sensor arrangement(s) may be used for implementing said first and second inspection modes, provided that the second inspection mode is less sensitive to geometric effects than the first inspection mode. In exemplary embodiments, the same sensor arrangement may be used to implement both inspection modes. In exemplary embodiments, a leading sensor arrangement may be used to trigger said second inspection mode in a trailing sensor arrangement.

The location of dented regions within the pipeline can be achieved via any suitable means, either as part of the same inspection run or an earlier inspection of the pipeline. Similarly, activation and deactivation of said secondary operating mode may be achieved via any suitable means. In exemplary embodiments, data from the sensors may indicate the presence of a dented region and thereby provide a trigger for activation and deactivation of the second operating mode.

Advantageously, primary and secondary inspection data sets are produced, which can be combined to provide a direct assessment of the presence of cracks and/or corrosion in wall material along a length of pipeline including one or more dented regions.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended and are understood to be within the scope of the claims.

Thus, while there has been shown and described and pointed out fundamental novel features of the invention as applied to exemplary embodiments thereof, it will be understood that various omissions and substitutions and changes in the form and details of the devices illustrated, and in their operation, may be made by those skilled in the art without departing from the spirit of the invention. Moreover, it is expressly intended that all combinations of those elements and/or method steps which perform substantially the same function in substantially the same way to achieve the same results are within the scope of the invention. Furthermore, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for pipeline inspection comprising:
providing a pipeline inspection apparatus configured for operating multiple inspection modes using sensors on the apparatus to provide inspection data relating to the presence of cracks and/or corrosion in wall material of a pipeline;
carrying out an inspection run in which a pipeline inspection apparatus travels inside a pipeline, wherein sensors on the apparatus are configured to conduct an in-line inspection of wall material along a length of the pipeline;
under normal operating conditions, using a first inspection mode to provide a primary inspection data set for the pipeline wall material upstream and downstream of a location of one or more dented regions;
selectively triggering a second inspection mode to provide a second inspection data set for the pipeline wall material as the apparatus travels through the one or more dented regions in the length of the pipeline wherein the second inspection mode is less sensitive to the geometric effects of the one or more dented regions than the first inspection mode; and
combining the primary inspection data set and the second inspection data set to provide a direct assessment for the presence of cracks and/or corrosion in wall material along the length of the pipeline, including along the one or more dented regions.

2. The method according to claim 1, wherein the first inspection mode comprises a short range scanning technique, and wherein the second inspection mode comprises a longer range scanning technique than the first inspection mode.

3. The method according to claim 1, wherein the second inspection data set comprises data relating to characteristics of the wall material in and substantially adjacent to the one or more dented regions of the pipeline, and wherein the second inspection mode is inactive as the apparatus travels along substantially undented regions of the length of the pipeline.

4. The method according to claim 1, further comprising:
determining the location of the one or more dented regions within a section of the pipeline;
using the first inspection mode when the apparatus is remote from the one or more dented regions;
triggering the second inspection mode when said apparatus approaches the location of the one or more dented regions;
using said second inspection mode when said apparatus is travelling through the one or more dented regions;
deactivating the second inspection mode after the apparatus has passed beyond the one or more dented regions; and
using the first inspection mode after the second inspection mode has been deactivated.

5. The method according to claim 1, wherein the location of the one or more dented regions is identified during the same inspection run.

6. The method according to claim 5, wherein the location of the one or more dented regions is identified with the sensors on the apparatus.

7. The method according to claim 6, wherein the identification of the one or more dented regions by the sensor acts as a trigger for activation of the second inspection mode.

8. The method according to claim 1, wherein the apparatus comprises a phased array of transducers for the first inspection mode.

9. The method according to claim 8, wherein the phased array is configured for operating the first and second inspection modes, wherein the first inspection mode has a different sensitivity to the geometric effects of dents than the second inspection mode.

10. The method according to claim 8, wherein the apparatus comprises at least one electro-magnetic acoustic transducer configured to generate guidedwaves in the second inspection mode.

11. The method according to claim 1, wherein the apparatus comprises a controller configured to control initiating the first inspection mode and the second inspection mode.

12. An apparatus for pipeline inspection configured to travel inside a pipeline, the apparatus comprising sensors for detecting the presence of cracks and/or corrosion in wall material of a pipeline, wherein the apparatus is configured with primary and secondary operating modes, wherein the primary operating mode uses a first mode of inspection to provide primary inspection data from the sensors, relating to the presence of cracks and/or corrosion in wall material along a length of pipeline, and wherein the apparatus further comprises a controller for controlling the secondary operating mode that uses a second mode of inspection, different to said first mode of inspection, to provide secondary inspection data from the sensors relating to the presence of cracks and/or corrosion in wall material along an axial length of pipeline, and wherein, if the primary operating mode is active, the apparatus is configured to trigger the secondary operating mode in response to a signal indicative that the apparatus is approaching one or more dented regions within a pipeline, and to deactivate the secondary operating mode in response to a signal indicative that the apparatus has travelled beyond the one or more dented regions and wherein the second inspection mode is less sensitive to the geometric effects of the one or more dented regions than the first inspection mode.

13. The apparatus according to claim 12, wherein the first inspection mode comprises a short range scanning technique, and wherein the second inspection mode comprises a longer range scanning technique than the first inspection mode.

* * * * *